US00PP25224P2

(12) United States Plant Patent
Misato

(10) Patent No.: US PP25,224 P2
(45) Date of Patent: Jan. 13, 2015

(54) ***MANDEVILLA* PLANT NAMED 'SUNPARA 3242'**

(50) Latin Name: *Mandevilla hybrida*
Varietal Denomination: Sunpara 3242

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 117 days.

(21) Appl. No.: 13/815,177

(22) Filed: Feb. 5, 2013

(51) Int. Cl.
*A01H 5/00* (2006.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Sunpara 3242', characterized by its upright and vining plant habit; vigorous growth habit; freely branching habit, dense and bushy plant form; dark green-colored leaves; freely flowering habit; long flowering period; and large light red purple-colored flowers.

1 Drawing Sheet

Botanical designation: *Mandevilla hybrida.*
Cultivar denomination: 'SUNPARA 3242'.

BACKGROUND OF THE INVENTION

The present invention relates to a new and distinct cultivar of *Mandevilla* plant, botanically known as *Mandevilla hybrida* and hereinafter referred to by the name 'Sunpara 3242'.

The new *Mandevilla* plant is a product of a planned breeding program conducted by the Inventor in Higashiomi, Shiga, Japan. The objective of the breeding program is to create new freely-branching and vining *Mandevilla* plants with numerous large attractive flowers.

The new *Mandevilla* plant originated from a cross-pollination in Higashiomi, Shiga, Japan in April, 2006 of a proprietary selection of *Mandevilla hybrida* identified as code number 02M11-1, not patented, as the female, or seed parent with a proprietary selection of *Mandevilla hybrida* identified as code number MH37-mt2, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in October, 2007.

Asexual reproduction of the new *Mandevilla* plant by cuttings in Higashiomi, Shiga, Japan since October, 2007 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpara 3242'. These characteristics in combination distinguish 'Sunpara 3242' as a new and distinct *Mandevilla* plant:

1. Upright and vining plant habit.
2. Vigorous growth habit.
3. Freely branching habit, dense and bushy plant form.
4. Dark green-colored leaves.
5. Freely flowering habit.
6. Long flowering period.
7. Large light red purple-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* have shorter lateral branches and internodes than plants of the female parent selection.
2. Plants of the new *Mandevilla* and the female parent selection differ in flower color as plants of the female parent selection have light pink-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are more vining and have longer internodes than plants of the male parent selection.
2. Plants of the new *Mandevilla* and the male parent selection differ in flower color as plants of the male parent selection have light pink-colored flowers.

Plants of the new *Mandevilla* can be compared to plants of the *Mandevilla* 'Sunparacore', disclosed in U.S. Plant Pat. No. 23,959. In side-by-side comparisons conducted in Higashiomi, Shiga, Japan, plants of the new *Mandevilla* differed from plants of 'Sunparacore' in the following characteristics:

1. Plants of the new *Mandevilla* had shorter lateral branches than plants of 'Sunparacore'.
2. Plants of the new *Mandevilla* had shorter internodes than plants of 'Sunparacore'.

3. Plants of the new *Mandevilla* had smaller leaves than plants of 'Sunparacore'.
4. Flower petals of plants of the new *Mandevilla* were narrower than flower petals of plants of 'Sunparacore'.
5. Plants of the new *Mandevilla* and 'Sunparacore' differed in flower color as plants of 'Sunparacore' had dark red-colored flowers.
6. Plants of the new *Mandevilla* had longer peduncles than plants of 'Sunparacore'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpara 3242' grown in a container.

The photograph at the bottom of the sheet is a close-up view of a typical flowering plant of 'Sunpara 3242'.

DETAILED BOTANICAL DESCRIPTION

The aforementioned photographs and following observations, measurements and values describe plants grown during the late summer and early autumn in 18-cm containers in an outdoor nursery in Higashiomi, Shiga, Japan and under cultural practices typical of commercial production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpara 3242'.

Parentage:

*Female, or seed, parent*.—Proprietary selection of *Mandevilla hybrida* identified as code number 02M11-1, not patented.

*Male, or pollen, parent*.—Proprietary selection of *Mandevilla hybrida* identified as code number MH37-mt2, not patented.

Propagation:

*Type*.—By vegetative cuttings.

*Time to initiate roots*.—About two weeks at 23° C. to 25° C.

*Time to produce a rooted young plant*.—About five to six weeks at 23° C. to 25° C.

*Root description*.—Fibrous; light brown in color.

*Rooting habit*.—Freely branching; medium density.

Plant description:

*Plant and growth habit*.—Upright and vining plant habit; vigorous growth habit; freely branching habit.

*Lateral branch description*.—Length: About 100 cm. Diameter: About 1.9 mm. Internode length: About 2.3 cm. Strength: Strong. Texture: Smooth, glabrous. Color: Close to 143B.

Foliage description:

*Arrangement*.—Opposite, simple.

*Length*.—About 4.9 cm.

*Width*.—About 3.1 cm.

*Shape*.—Ovate.

*Apex*.—Mucronate.

*Base*.—Obtuse.

*Margin*.—Entire.

*Texture, upper and lower surfaces*.—Smooth, glabrous.

*Venation pattern*.—Pinnate, reticulate.

*Color*.—Developing leaves, upper surface: Close to 143A. Developing leaves, lower surface: Close to 143C. Fully expanded leaves, upper surface: Close to N137A; venation, close to 144B. Fully expanded leaves, lower surface: Close to 137C; venation, close to 144C.

*Petiole length*.—About 1.5 cm.

*Petiole diameter*.—About 1.3 mm.

*Petiole texture, upper and lower surfaces*.—Smooth, glabrous.

*Petiole color, upper and lower surfaces*.—Close to 143A.

Flower description:

*Flower type and habit*.—Single salverform flowers arranged in axillary racemes; flowers face upright to outwardly; freely flowering habit with about three to eight flowers per inflorescence.

*Natural flowering season*.—Plants begin flowering about six weeks after planting; long flowering period, plants flower continuously from early summer to late autumn in Japan.

*Flower longevity on the plant*.—About seven to ten days; flowers not persistent.

*Fragrance*.—None detected.

*Inflorescence height*.—About 13.4 cm.

*Inflorescence diameter*.—About 13.1 cm.

*Flowers*.—Appearance: Salverform; flared trumpet, corolla fused and five-parted; flowers roughly star-shaped. Diameter: About 7.6 cm. Depth (length): About 6.9 cm. Throat diameter: About 1.7 cm. Tube length: About 4.7 cm. Tube diameter, mid-section: About 1.1 cm. Tube diameter, base: About 3.5 mm.

*Flower buds*.—Height: About 6.4 cm. Diameter: About 1.2 cm. Shape: Lenticular. Color: Close to 53B.

*Corolla*.—Quantity and arrangement: Five petals arranged in a single whorl and fused towards the base into an elongated tube. Petal lobe length: About 3.5 cm. Petal lobe width: About 2.6 cm. Petal lobe shape: Obovate. Petal lobe apex: Cuspidate. Petal lobe margin: Entire. Petal lobe texture, upper and lower surfaces: Smooth, glabrous. Throat texture: Smooth, glabrous. Tube texture: Smooth, glabrous. Color: Petal lobe, when opening, upper surface: Close to N57A. Petal lobe, when opening, lower surface: Close to 58A. Petal lobe, fully opened, upper surface: Close to N57B. Petal lobe, fully opened, lower surface: Close to 53D. Throat: Towards the petal, close to 53B; towards the base, close to 25A. Tube: Towards the apex, close to 51A; mid-section, close to 26C; towards the base, close to N34A.

*Calyx*.—Quantity and arrangement: Five sepals arranged in a single whorl; calyx, star-shaped. Sepal length: About 1 cm. Sepal width: About 1.8 mm. Sepal shape: Deltoid. Sepal apex: Acute. Sepal base: Truncate. Sepal margin: Entire. Sepal texture, upper and lower surfaces: Smooth, glabrous. Sepal color: When developing, upper surface: Close to 145A tinted with close to 47A. When developing, lower surface: Close to 145B. Fully developed, upper and lower surfaces: Close to 145C tinted with close to 47B.

*Peduncles*.—Length: About 6.25 cm. Diameter: About 2 mm. Texture: Smooth, glabrous. Aspect: Upright to outwardly. Color: Close to 144B.

*Pedicels*.—Length: About 1.8 cm. Diameter: About 2.1 mm. Texture: Smooth, glabrous. Aspect: Upright to outwardly. Color: Close to 144B.

*Reproductive organs*.—Stamens: Quantity and arrangement: Typically five; filaments fused to corolla; anthers, connivent. Anther shape: Ellipsoidal. Anther length: About 1 cm. Anther color: Close to 8A. Pollen amount: Moderate. Pollen color: Close to 4D. Pistils: Quantity: Typically one. Pistil length: About 2.6 cm. Style color: Close to 145D. Stigma shape: Conical. Stigma color: Close to 145C. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpara 3242' as illustrated and described.

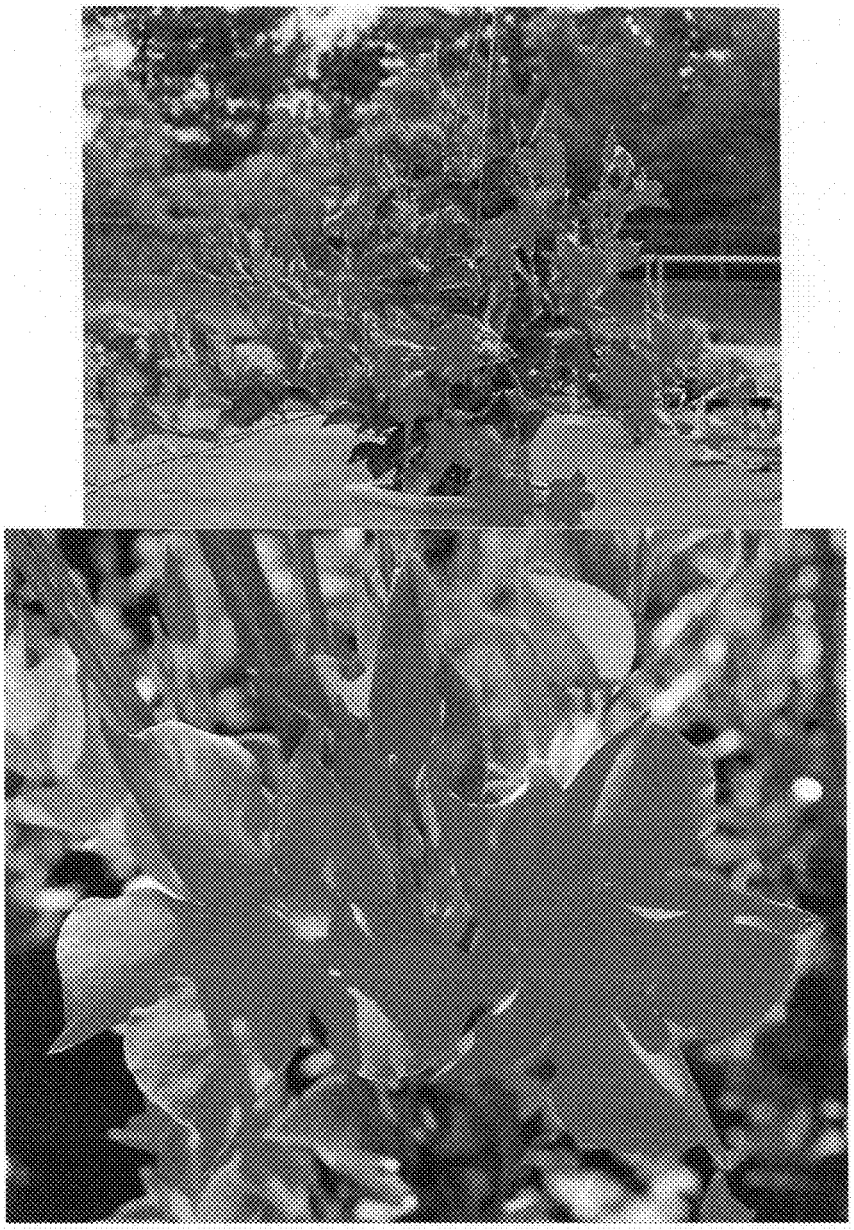

* * * * *